United States Patent [19]
Wise

[11] Patent Number: 6,082,995
[45] Date of Patent: Jul. 4, 2000

[54] OCCLUSAL PREFORM AND PROCEDURE FOR PRODUCING DENTAL SPLINT APPLIANCES

[76] Inventor: Thomas B. Wise, 2568 Cheyenne Pl., Saginaw, Mich. 48603

[21] Appl. No.: 08/901,891

[22] Filed: Jul. 29, 1997

[51] Int. Cl.[7] .................................................. A61C 3/00
[52] U.S. Cl. ............................ 433/6; 433/214; 128/861
[58] Field of Search ...................... 433/6, 214; 206/63.5, 206/83; 128/861, 862

[56] References Cited

U.S. PATENT DOCUMENTS

| Re. 35,034 | 9/1995 | Albert | 206/63.5 |
|---|---|---|---|
| 3,178,820 | 4/1965 | Kesling | 433/6 |
| 3,303,844 | 2/1967 | Johnson et al. | 433/6 |
| 3,407,500 | 10/1968 | Kesling | 433/6 |
| 3,898,736 | 8/1975 | Bergersen | 433/6 |
| 3,939,598 | 2/1976 | Bergersen | 433/6 |
| 4,184,255 | 1/1980 | Gordon | 433/6 |
| 4,371,336 | 2/1983 | Hilleman | 433/6 |
| 4,881,713 | 11/1989 | Wise . | |
| 5,063,940 | 11/1991 | Adell et al. | 206/63.5 |

*Primary Examiner*—Ralph A. Lewis
*Attorney, Agent, or Firm*—Reising, Ethington, Barnes, Kisselle, Learman & McCulloch P.C.

[57] ABSTRACT

An occlusal splint is prepared by forming a wax pattern of a patient's bite corresponding to a desired occlusal spacing and fitting the pattern to working models of the patient's jaw teeth to duplicate the spacing in the models. A splint preform of light-curable octadecyl methacrylate composite material is applied to the model after which the occlusal impression is duplicated in the preform. The preform is then cured under high intensity light and then polished to complete the finished splint.

12 Claims, 4 Drawing Sheets

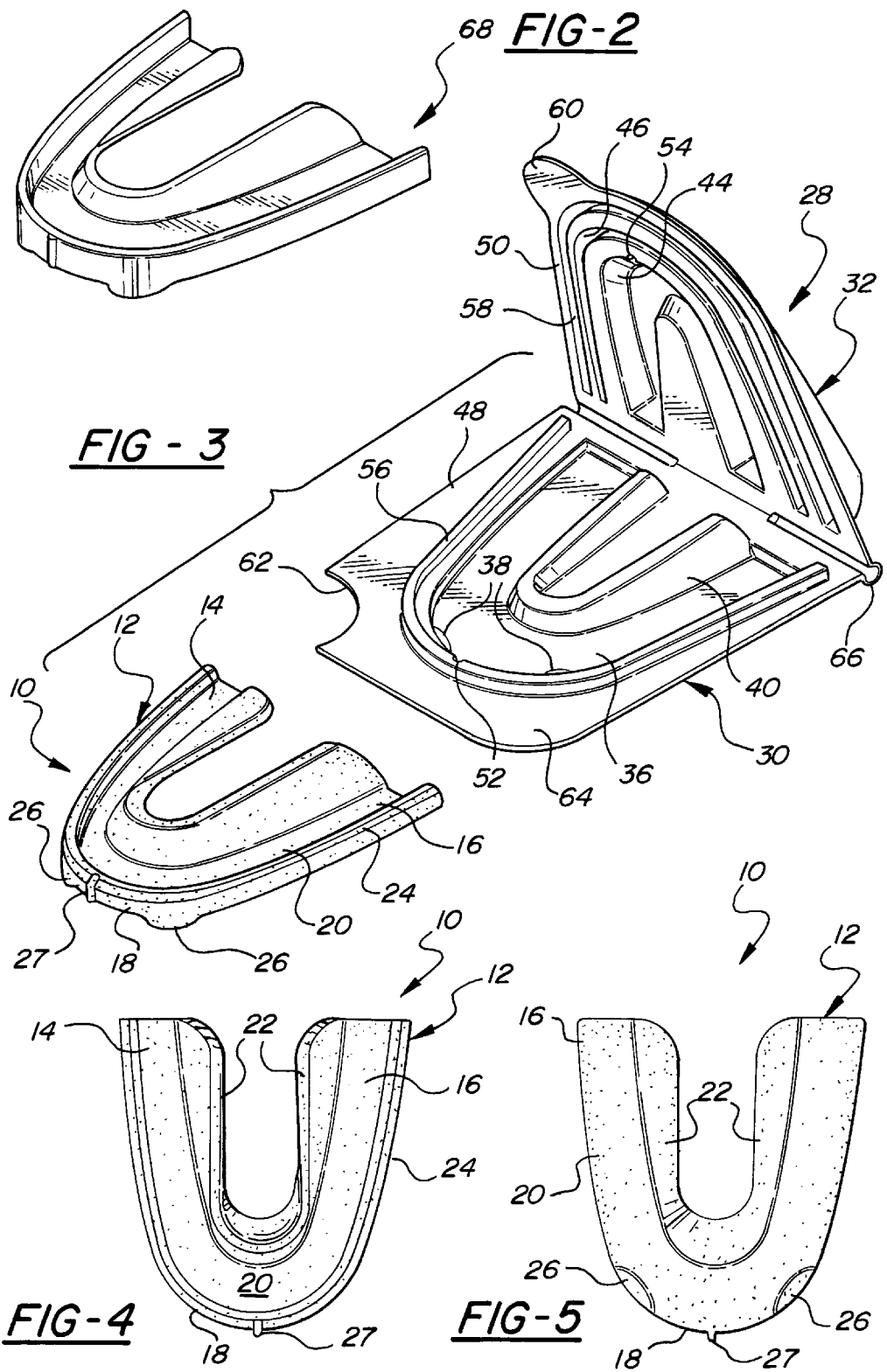

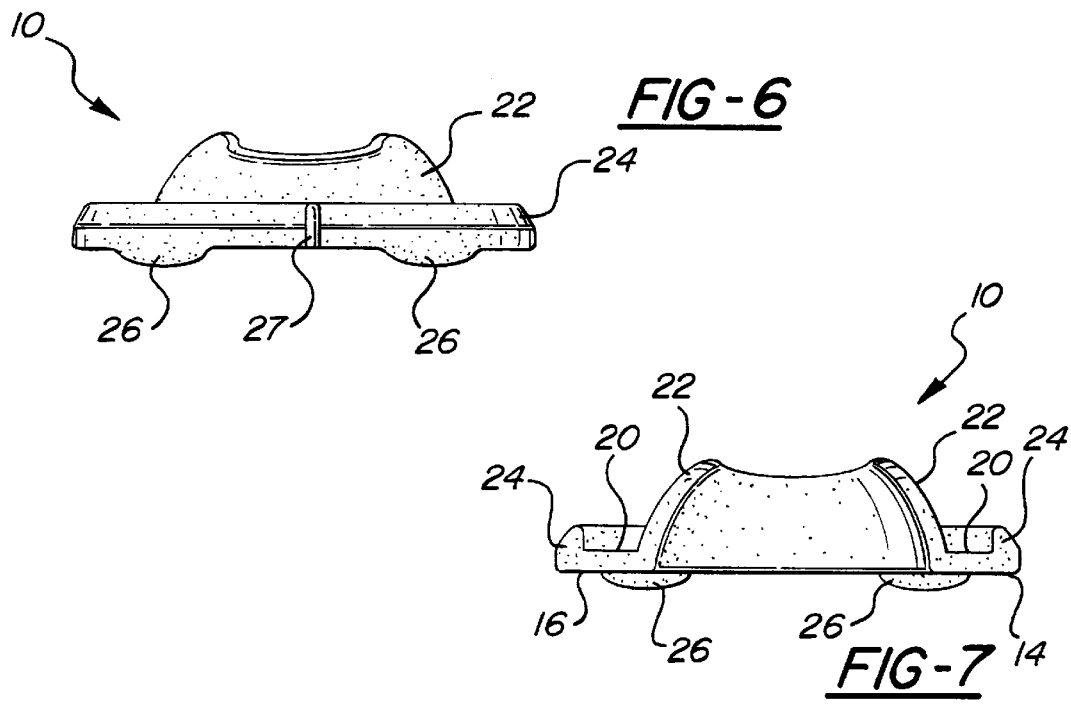
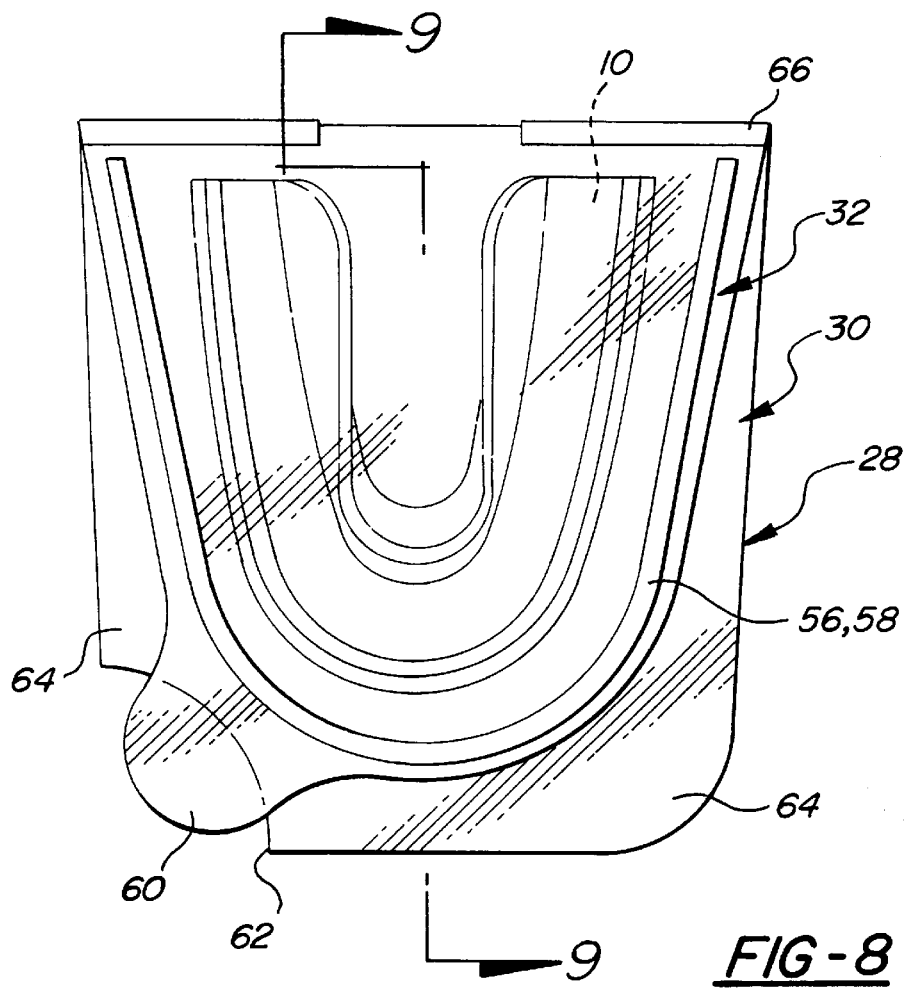

OCCLUSAL PREFORM AND PROCEDURE FOR PRODUCING DENTAL SPLINT APPLIANCES

This invention relates to procedures and materials used by dentists and dental technicians in the making of dental splints.

BACKGROUND OF THE INVENTION

It is known to use occlusal splints for treatment of various kinds of disorders to relieve strain on the temporal mandibular joint.

My earlier U.S. Pat. No. 4,881,713, issued Nov. 21, 1989, describes a procedure presently in use for making such dental splints. It involves the molding of a preform pattern from dental wax or other suitable material that is form-stable at room temperature and flowable at elevated temperatures having a generally U-shaped trough configuration that approximates a patient's bite. The pattern is heated a few degrees above normal human body temperature and placed in the mouth of the patient after which the patient's mouth is closed to a desired occlusal spacing which imparts a corresponding occlusal impression in the wax pattern. The wax pattern is then placed in an investment mold and invested, following which it is removed and replaced by acrylic material which is cast, heat-cured, and then polished to form the finished splint.

Such heat-cured splints are often fabricated from methyl-methacrylate and a powder mixture that, once invested, is cured under pressure in a hot water bath. The time for heat-curing such splints is on the order of about twelve hours, making it difficult for a dentist or technician to complete the entire procedure in a single day. For those dentists who do not have an investment caster at their disposal, it is common for them to send the wax pattern to a laboratory to cast the splint, which can further delay the process by several days or weeks. In either case, it requires at least one return visit by the patient, adding to the cost and inconvenience of the procedure.

Another disadvantage with heat-cured acrylic splints is that a certain amount of residual monomer has been found to remain in the acrylic after curing, causing for some patients a irritation or allergenic reaction with the tissues of the mouth. In severe cases, the patient is no longer able to wear the splint.

The present invention overcomes or greatly minimizes all of the foregoing objections.

SUMMARY OF THE INVENTION

Models are taken of a patient's maxillary and mandibular jaw teeth and are mounted on an articulator and adjusted to achieve a desired occlusal spacing of the models. This step is achieved preferably with the assistance of a wax preform pattern which is softened and placed in the patient's mouth to obtain an occlusal imprint in the pattern corresponding to the desired occlusal spacing of the patient. The imprinted wax pattern is transferred to the models and the articulator adjusted to align the teeth of the models with the imprint of the pattern, thereby duplicating the desired spacing in the models. The wax pattern is then removed and discarded.

Following the proper adjustment of the models, a separate preform is used to produce the occlusal splint. This latter preform comprises a generally U-shaped trough member similar in shape to the wax pattern preform, but fabricated of a light-curable composite material in an uncured state in which the material is sufficiently plastic and flowable to permit an impression to be made in the preform. In the preferred embodiment, the preform is supplied pre-packaged in a compartment of a plastic carrier that conforms closely to the size and shape of the preform to support it in its preform shape until ready to use. To use the preform, the technician or dentist opens the carrier and removes the uncured preform from the compartment and places the preform on a selected one of the working models. The articulator is then repositioned to the desired occlusal spacing position to duplicate the occlusal impression in the preform. The preform is then exposed to a predetermined light curing cycle to cure the preform and generate the finished occlusal splint.

The light-curable preform eliminates the need for costly investment casting equipment or outside laboratory services associated with the making of heat-curable acrylic splints. The cure time is on the order of minutes rather than hours and requires no special equipment other than a light-curing unit which many dentists have on hand for other purposes. The short cycle time enables a dentist or technician to perform the entire procedure in his office and to complete the splint while the patient waits. This eliminates the need for a return visit by the patient and saves time for the dentist.

The entire procedure easily can be performed by dental office support staff with minimal training, thereby enabling the dentist to perform other procedures. The quick cure cycle further makes the preform of the invention less prone to shrinkage as compared to the heat-cured counterparts, resulting in a better fit in its cured state and minimizing time consuming post-cure adjustments.

Another important advantage that the light-curable preform has over its heat-cured counterpart is that the material from which the preform is made is stable in its cured state and does not contain or release residual monomers that can cause tissue irritation. Thus, a dental splint appliance made from the light-curable preform of the invention can be worn by all patients, including those who could not otherwise wear a heat-cured acrylic splint.

THE DRAWINGS

Methods and apparatus according to a preferred embodiment of the invention are disclosed in the following description and in the accompanying drawings, wherein:

FIG. 2 is a perspective view of a wax preform pattern used in the procedure;

FIG. 3 is a perspective, exploded view of the splint preform and associated carrier;

FIGS. 4 and 5 are top and bottom plan views, respectively, of the splint preform;

FIGS. 6 and 7 are front and back elevational views, respectively, of the splint preform;

FIG. 8 is a top plan view of the carrier in the closed position supporting the splint preform therein;

DETAILED DESCRIPTION

Figure 1:
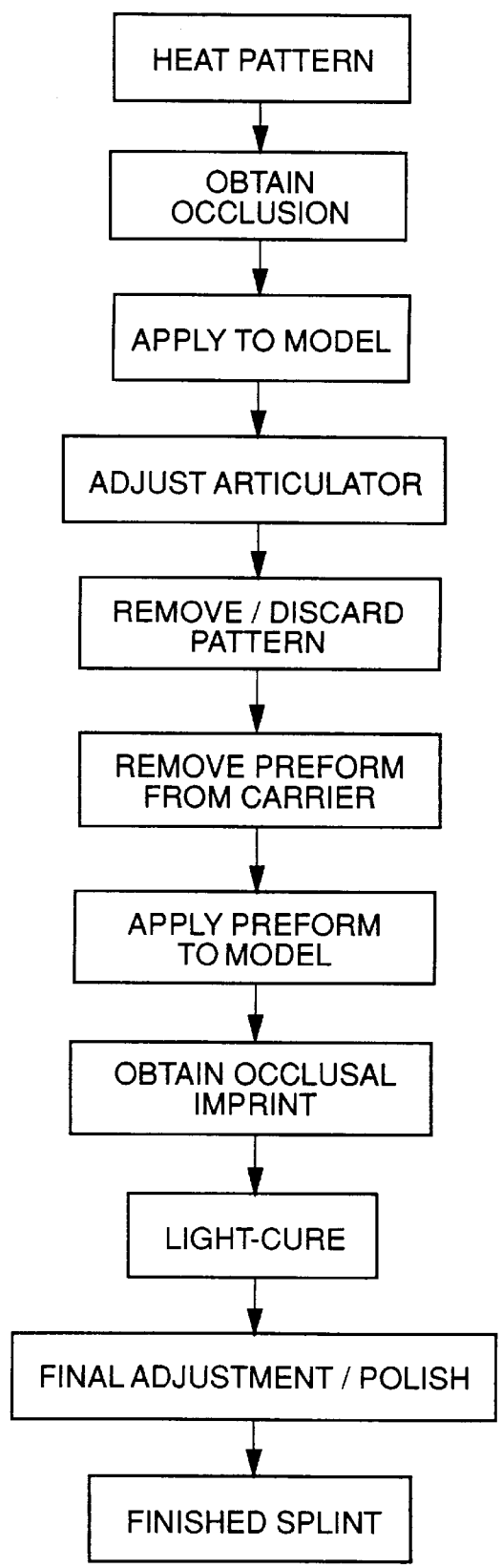
FIG. 1 is a flow chart illustrating the steps involved in making a splint according to the invention.

An occlusal splint preform constructed according to a presently preferred embodiment of the invention is designated generally by the reference numeral 10 in FIGS. 3–9 and comprises a generally U-shaped trough member 12 having spaced apart limbs 14, 16 converging in a direction toward one end of the member 12 and being joined at such end by an arcuate bight 18. The member 12 has a base 20 that is generally planar and U-shaped in plan and has a width that intentionally is greater than that of a patient's teeth enabling the preform to accommodate a wide range of bites that may vary considerably among different patients. Spaced apart, upstanding inner and outer sidewalls 22, 24 extend in the same general direction from the inner surface of the base 20. The base 20 and the sidewalls 22 and 24 are of generally uniform thickness except for a pair of cuspid risers 26 protruding from the outer surface of the base 20 at positions corresponding to those of a person's cuspids, as illustrated best in FIGS. 3, 5 and 6. As shown in FIGS. 6 and 7, the height to which the inner sidewall 22 extends above the base 20 is substantially greater than that of the outer sidewall 24. The inner sidewall 22 has a height of about 0.45 inch whereas the outer sidewall has a height of about 0.06 inch. The inner sidewall 22 forms an obtuse included angle with the base 20 approximating the arch of the maxillary or mandibular jaw of a patient, and is preferably in the range of about 110 to 130 degrees.

The outer sidewall 24 is formed with a frontal alignment ridge 27 at the midpoint of the bight 18 which preferably extends the full height of the outer wall and has a width that preferably does not exceed about 1 mm.

The preform 10 is fabricated from a material that is relatively soft and readily deformable in its uncured state to enable it to conform under pressure to the shape of a patient's mouth and imprint the teeth of the patient on the preform. Further details concerning the preferred material of the preform 10 are given below.

A carrier of the invention associated with the preform 10 is designated generally by the reference numeral 28 in FIG. 3 and comprises a vacuum formed plastic tray member having separable base 30 and lid 32 portions contoured to provide a cavity or compartment 34 therebetween when the lid 32 is closed upon the base 30 (FIG. 9), having a size and shape corresponding substantially and preferably identically to the size and shape of the preform 10. The base 30 of the carrier 28 has a generally planar U-shaped recess 36 corresponding to the base 20 of the preform 10 and includes a pair of indentations 38 to accommodate the cuspid risers 26 of the preform 10. An upwardly protruding, arcuate wall 40 of the base 30 corresponds to the innermost side of wall 22 of the preform 10. The lid 32 includes an arcuate recess 42 that receives the protusion 40 of the base 30 and has an arcuate wall 44 corresponding to the outermost surface of the wall 22 of the preform. Outwardly of the recess 42 is another, shallower U-shaped recess 46 corresponding to the outer sidewall 24 of the preform 10.

Figure 9:
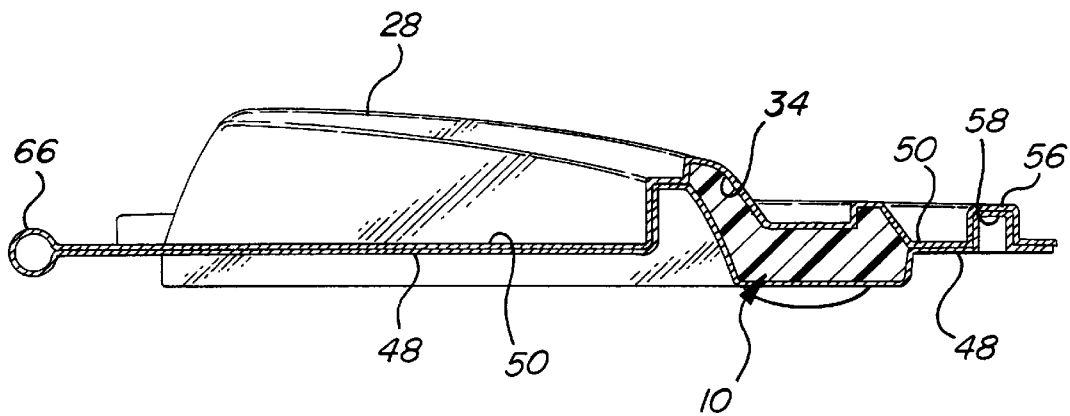
FIG. 9 is a sectional view taken on the line 9—9 of FIG. 8.

Extending beyond the compartment 34 are generally planar flange portions 48, 50 of the base 30 and lid 32, respectively, whose confronting surfaces contact one another when the lid 32 is closed upon the base 30, as shown in FIG. 9. The recesses 36, 46 are provided with aligned indentations 52, 54 corresponding to the frontal alignment ridge 27 of the preform 10.

The carrier 28 preferably has releasable locking means for securing the base 30 and lid 32 in the closed position but enabling separation of the base 30 and lid 32. The preferred locking means comprises unitary latching portions of the base and lid which engage and interlock when the lid 32 is closed on the base 30. The preferred interlocking structure comprises a generally U-shaped rib 56 molded into the flange of either the base or lid outwardly of compartment 34, and a corresponding U-shaped channel 58 formed in the flange of the other of the base or lid members in aligned relation with the rib 56. The rib 56 and channel 58 are so dimensioned that a frictional fit is provided upon pressing the rib 56 into the channel 58 sufficient to resist separation of the base and lid members until a bodily separation force is applied to the carrier. If desired, the parts 56 and 58 may be crimped as at 59 (FIG. 8) to assist in sealing and latching the base and lid. In addition to locking the base and lid members together, the rib and channel also serve to align the base 30 of the compartment properly with the lid 32.

As illustrated best in FIG. 8, the flange 50 of the lid 32 has a tab portion 60 that, when the carrier is closed, overlies an underlying cutout portion 62 of the base flange 48. At least a portion 64 of the base flange 48 extends beyond the flange 50 of the lid. The portions 60, 64 provide a convenient location to grasp and open the carrier 28 to gain access to the compartment 34.

The base 30 and lid 32 are preferably vacuum formed from a single piece of plastic sheet material and joined along a common edge by a unitary hinge portion 66 which enables the base and lid to hinge between the open and closed positions. The carrier material has a preferred thickness of about 0.010 inch and is preferably transparent or translucent.

It is preferred that the splint preform 10 be supplied to the technician or dentist prepackaged in the carrier 28. In this way, the preform 10 is able to retain its shape prior to use and is protected against contamination.

An additional advantage that the carrier 28 provides is that it can serve as an inexpensive mold in the initial formation of the preform 10. Relatively unskilled persons can prepare the preform 10 by simply laying a quantity of the uncured preform material into the compartment, closing the base 30 onto the lid 32, and then applying pressure to the outer surface of the carrier 28 to mold the preform material to the shape of the compartment 34. The carrier 28 then may be opened to remove any flash and reclosed to contain the preform 10 unit ready for use.

It will be understood that the splint preform 10 need not be molded directly in the compartment 34 of the carrier 28 by the manual molding technique disclosed, but may be premolded to shape in a separate mold of a more permanent nature and then transferred to the compartment 34 for support and protection until ready for use.

The preform 10 is preferably fabricated from a light-curable (or photo-curable) polymer, preferably a urethane methacrylate composite. A suitable material is an octadecyl methacrylate composite having an interpenetrating organic filler, organic silica fillers, and photo initiators of the type manufactured by Heraeus Kulzer, Inc. (Kulzer) of Irvine, Calif. under the trademark "Palasplint". In its cured state this material does not retain any residual monomers that cause irritation to the tissues of a person's mouth.

It is preferable to use a release agent in the compartment 34 of the carrier 28 to assist in a release of the preform 10 upon its removal from the carrier 28 at time of use. Such release agents are well known.

To prepare an occlusal splint according to a preferred procedure of the invention, working models (not shown) are first made of the patient's maxillary and mandibular jaw teeth according to conventional practice. The models are mounted in an articulator (not shown) as is customary and the models adjusted to provide therebetween a desired occlusal spacing or centric opening representing that which the occlusal splint is to provide when worn by the patient.

To obtain the desired occlusal spacing, an impression of the patient's bite is first made, preferably by means of a wax pattern 68 (FIG. 2) prepared in accordance with my earlier U.S. Pat. No. 4,881,713, the disclosure of which is incorporated herein by reference. As taught therein, the pattern 68 is heated to soften the material and then placed in the user's mouth after which the patient's mouth is closed to the desired occlusal spacing forming a corresponding imprint of the user's teeth upon the pattern 68. According to the present invention, pattern 68 is positioned between the models and the articulator adjusted to register the teeth of the model with the imprint on the pattern 68, thereby duplicating the occlusal spacing in the models. Once adjusted, the articulator is locked by an incisal pin in known manner to retain the adjusted relation of the models. The wax pattern 68 is then removed and may be discarded.

The model corresponding to teeth of the patient on which the splint is to be worn is then removed from the articulator and any undercuts on the model blocked out by building up those areas with putty. A release agent is then applied to the model in preparation to receive the splint preform 10. Once the model is prepared, the splint preform 10 is removed from its carrier, placed on the model so that the frontal ridge 27 is aligned with the midline of the model, and then molded or manipulated by hand into conformance with the general contours of the teeth of the model. The model is then remounted on the articulator and repositioned to the desired occlusal spacing provided by the base 20 to duplicate the occlusal imprint of the models on the uncured preform 10, including the formation of cuspid impressions in the cuspid risers 26 of the preform 10. Any excess preform material 10 is trimmed.

Figure 10:
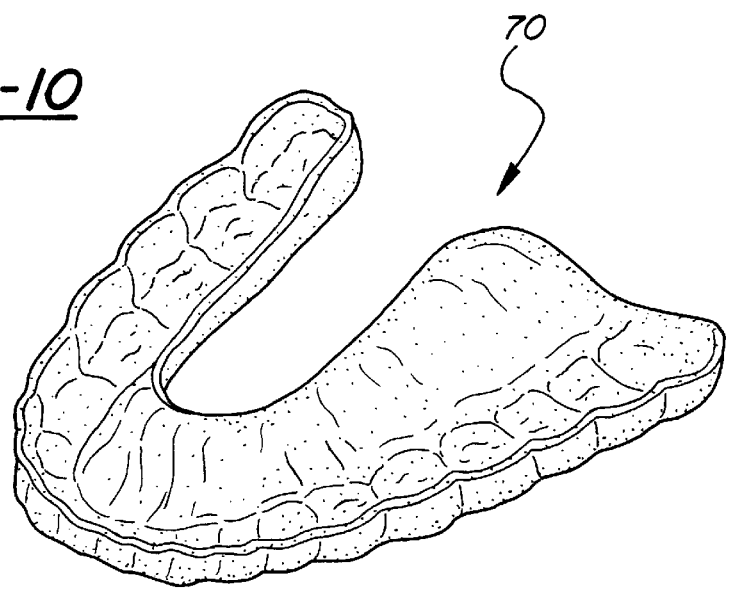
FIG. 10 is a perspective view of the finished splint.

When trimming is complete and the desired occlusal bite established, the model is again removed from the articulator and placed, together with the imprinted preform 10, in a chamber of a known light curing unit (not shown) and irradiated with high intensity curing light which reacts with and cures the preform 10. The preform 10 is then removed from the light-cure unit, removed from the model, final fitted and polished to produce a finished occlusal splint appliance 70, like that illustrated in FIG. 10. The cured splint 70 has sufficient hardness and strength to retain its shape when worn by the patient, and is comparable to the strength and durability of heat-cured acrylic splints currently in use.

The strength and intensity of the curing light will govern the time of the curing cycle. The preferred light cure unit is the UNIXS unit manufactured and sold by Kulzer. This unit has a chamber sized to accommodate the model and preform and a high intensity light which fully cures the preform in about 90 seconds. The curing process photo-polymerizes the preform material causing it to become rigid and form-stable.

While the specific light-curable preform material and light-curing unit described above are preferred, those skilled in the art will understand that other light-curing units could be used but, depending on the intensity of the curing light, may take more time than that of the preferred unit to cure the preform. Available lower power light-curing units, for example, may take upwards of 15 minutes for a complete cure of the preform material which is still substantially less than the curing time required for a comparable heat-cured splint.

The disclosed embodiment is representative of a presently preferred form of the invention, but is intended to be illustrative rather than definitive thereof. The invention is defined in the claims.

I claim:

1. A method of making an occlusal dental splint comprising:
   a. forming a model of a patient's maxillary and mandibular arches and the respective teeth thereof;
   b. obtaining a U-shaped splint preform formed from an uncured, deformable, light-curable substance, said preform having a pair of limbs converging toward corresponding ends thereof and being joined at said ends by an arcuate bight, said preform having a pair of upstanding side walls joined by a substantially planar base, said base and said side walls together forming a trough, said base having a thickness corresponding substantially to the occlusal space to be provided between the patient's maxillary and mandibular jaw teeth;
   c. placing said preform in a position in which said trough embraces the teeth of a selected one of the arches of said model and occupies a position in which the side walls extend alongside the teeth of said one of said arches and one surface of the base confronts and overlies the teeth of said one of said arches;
   d. manipulating and deforming said preform to cause said side walls of said trough to conform substantially to the configurations of the sides of the teeth embraced by said trough and the teeth embraced by said trough to form an impression in said one surface of said base of said trough;
   e. and exposing said preform following the performance of steps a, b, c, and d above to a curing light for a sufficient period of time to cure said substance, said substance when cured having sufficient rigidity and stability to maintain its cured shape when inserted in the patient's mouth with said base in a position between such patient's maxillary and mandibular arches.

2. The method of claim 1 including curing the splint preform in place on the model to which it is applied.

3. The method of claim 1 including using a light-curable methacrylate composite as the splint preform material.

4. The method of claim 1 including using a light-curable octadecyl methacrylate composite as the splint preform material.

5. The method of claim 1 including supporting the splint preform prior to use in its uncured state within an accessible compartment of a separable carrier, said compartment conforming substantially in shape to that of the preform.

6. A method of producing an occlusal dental splint comprising:
   a. positioning a preformed wax pattern in the mouth of a patient in a position between the patient's maxillary and mandibular arches;
   b. closing the patient's mouth to obtain an occlusal impression of the patient's teeth in the pattern corresponding to a desired occlusal spacing between the maxillary and mandibular jaw teeth of the patient;
   c. removing the pattern from the mouth of the patient and placing the pattern between working models of the maxillary and mandibular arches of the patient;
   d. registering the teeth of the models to the occlusal impression of the pattern thereby duplicating the desired occlusal spacing between the models;
   e. removing the pattern from between the models;
   f. applying a splint preform fabricated of uncured, light-curable, deformable material to the teeth of a selected one of said arches, said preform having a pair of spaced apart side walls joined by a base, said side walls and said base together forming a trough which embraces the teeth of the selected one of said arches with said base having a surface overlying and confronting the teeth of the selected one of said arches;

g. repositioning the models to said desired occlusal spacing position thereby enabling the teeth of the selected one of said arches to duplicate said occlusal impression in said surface of the base of the splint preform;

h. manipulating and deforming the side walls of the trough of the splint preform to conform said side walls and said surface of said base to the teeth of said selected one of said arches;

i. placing said selected one of the arches and the preform in a chamber of a light curing device; and j. activating the device to light-cure the preform.

7. The method of claim 6 including using a splint preform fabricated of a light-curable methacrylate material.

8. An occlusal dental splint preform and container construction comprising:

a. an occlusal splint preform composed of an uncured, light curable substance which in its uncured state is form stable but sufficiently plastic to be shaped to conform generally to the configuration of a person's maxillary or mandibular arch, said preform having spaced apart side walls joined by a base, said side walls and said base together forming a trough of such size and shape as to embrace the teeth of a selected one of the person's maxillary or mandibular arch with the base of said trough overlying and confronting the teeth of said selected arch; and b. a container having two parts which together define a compartment corresponding substantially to the size and shape, including said trough, of said preform, the two parts of said container being separable to enable said preform to be removed from said compartment.

9. The construction according to claim 8 including releasable latch means releasably latching said parts of said container in said closed position.

10. The construction according to claim 9 wherein said latch means comprises interlocking ridge and channel portions on said two parts of said container.

11. The construction according to claim 8 including a hinge connecting said two parts of said container to one another for hinging movements between two positions in one of which said compartment is closed and in the other of which said compartment is open.

12. The construction according to claim 11 wherein said hinge is a unitary component of said two parts of said container.

* * * * *